(12) United States Patent
Sullivan

(10) Patent No.: US 11,096,788 B2
(45) Date of Patent: Aug. 24, 2021

(54) HINGED ARTICULATING SPACER SYSTEM FOR REVISION KNEE ARTHROPLASTY

(71) Applicant: Donald N. Sullivan, Decatur, IL (US)

(72) Inventor: Donald N. Sullivan, Decatur, IL (US)

(73) Assignee: Donald N. Sullivan, Decatur, IL (US)

( * ) Notice: Subject to any disclaimer, the term of this patent is extended or adjusted under 35 U.S.C. 154(b) by 114 days.

(21) Appl. No.: 16/551,378

(22) Filed: Aug. 26, 2019

(65) Prior Publication Data

US 2020/0113701 A1 Apr. 16, 2020

Related U.S. Application Data

(60) Provisional application No. 62/743,994, filed on Oct. 10, 2018.

(51) Int. Cl.
   *A61F 2/38* (2006.01)
   *A61F 2/46* (2006.01)
   *A61F 2/30* (2006.01)

(52) U.S. Cl.
   CPC .............. *A61F 2/384* (2013.01); *A61F 2/461* (2013.01); *A61F 2/389* (2013.01); *A61F 2/3859* (2013.01); *A61F 2002/30624* (2013.01); *A61F 2002/30672* (2013.01); *A61F 2002/4615* (2013.01); *A61F 2310/00353* (2013.01)

(58) Field of Classification Search
   CPC ............ A61F 2/384; A61F 2002/30624; A61F 2/461; A61F 2002/4615; A61F 2/3859; A61F 2/389; A61F 2002/30621
   See application file for complete search history.

(56) References Cited

U.S. PATENT DOCUMENTS

| 3,909,854 A * | 10/1975 | Martinez ................. A61F 2/384 623/20.26 |
| 6,019,794 A * | 2/2000 | Walker ..................... A61F 2/385 623/20.22 |
| 2014/0288659 A1* | 9/2014 | Vogt .......................... A61F 2/38 623/20.31 |

* cited by examiner

*Primary Examiner* — David H Willse
*Assistant Examiner* — Javier G Blanco
(74) *Attorney, Agent, or Firm* — Stinson LLP

(57) ABSTRACT

A hinged articulating spacer system for revision knee arthroplasty includes a femur rod for a femur, and a tibia rod for a tibia. The tibia rod is hingedly couplable to the femur rod to form a hinged rod assembly. A pre-formed femoral spacer component includes bone cement impregnated with an antibiotic. The pre-formed femoral spacer defines an opening that receives the hinged rod assembly. A pre-formed tibial spacer component includes bone cement impregnated with an antibiotic. The pre-formed tibial spacer defines an opening that receives the hinged rod assembly.

16 Claims, 13 Drawing Sheets

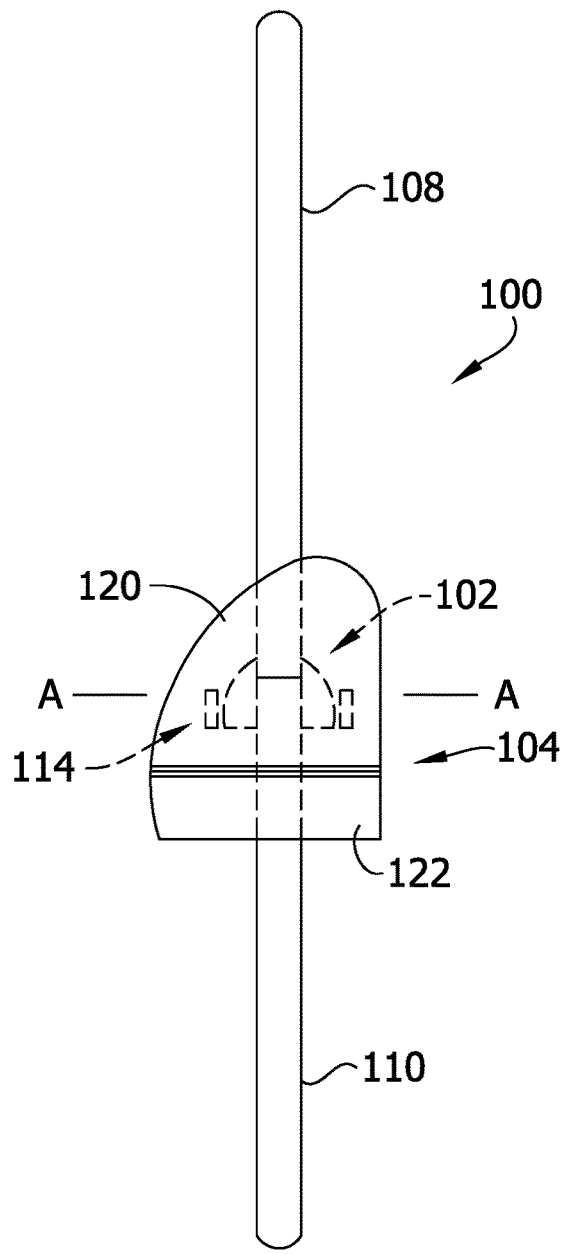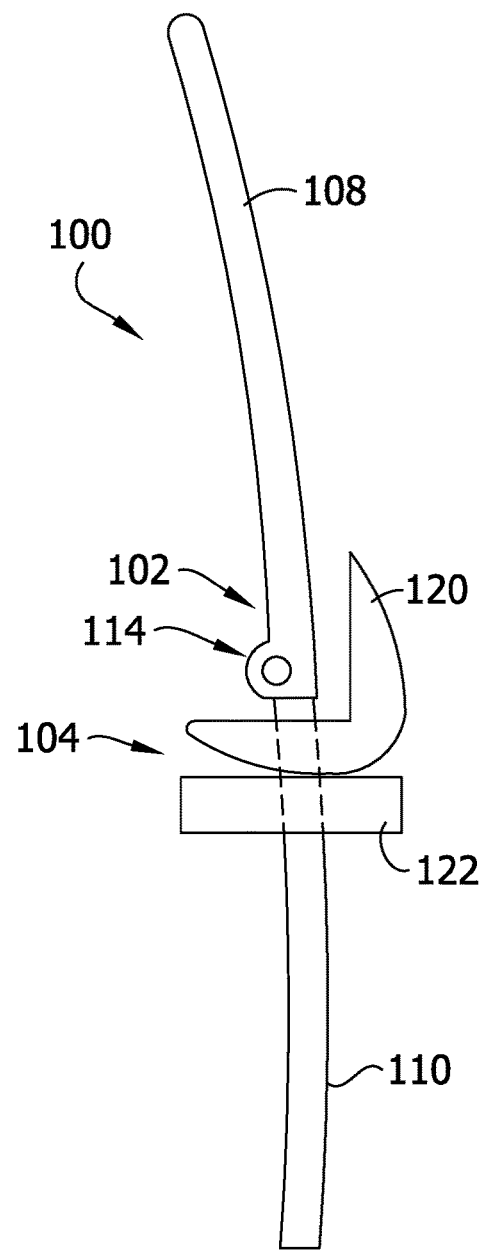

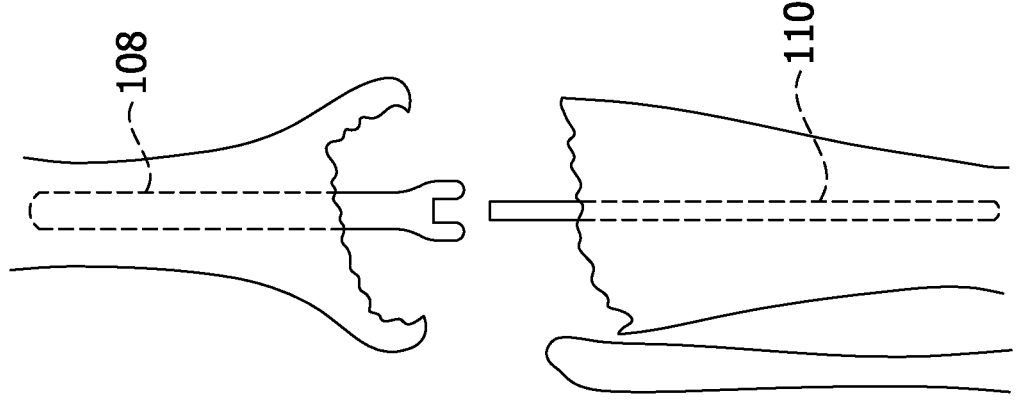
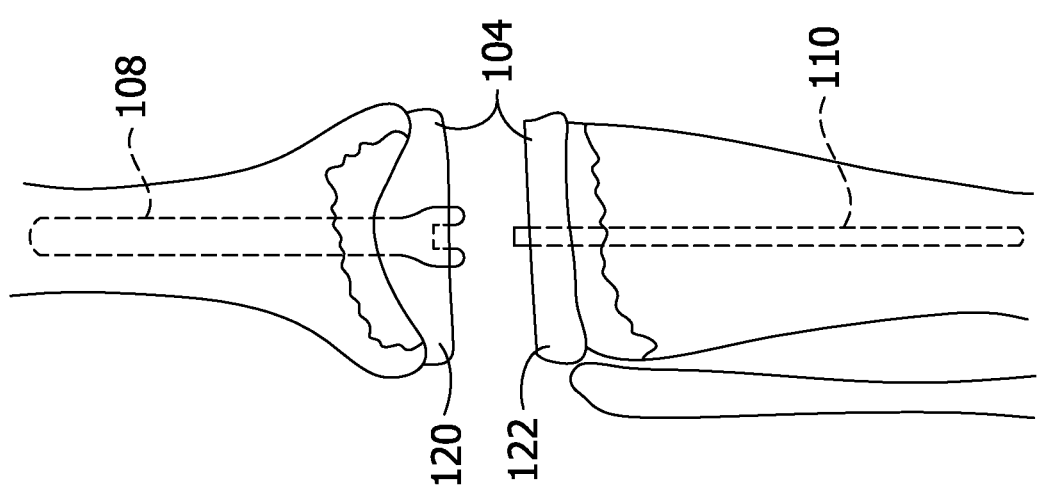
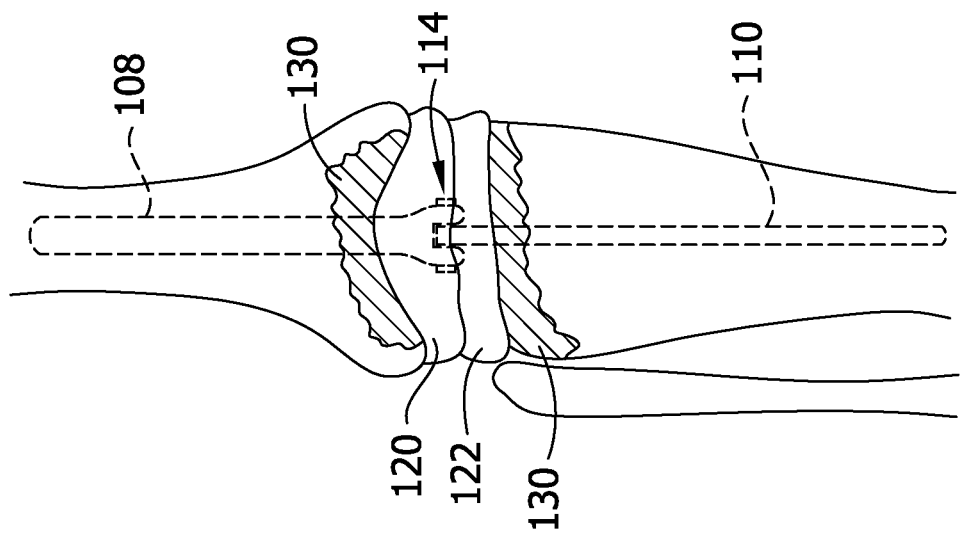

HINGED ARTICULATING SPACER SYSTEM FOR REVISION KNEE ARTHROPLASTY

CROSS-REFERENCE TO RELATED APPLICATIONS

The present application claims the benefit of U.S. Provisional Application Ser. No. 62/743,994, filed Oct. 10, 2018, the entirety of which is hereby incorporated by reference.

FIELD OF THE DISCLOSURE

The present disclosure generally relates to a hinged articulating spacer system for revision knee arthroplasty.

BACKGROUND OF THE DISCLOSURE

Revision total knee arthroplasty (TKA) may be performed when total knee prosthesis becomes infected, for example. One type of revision TKA is performed in two operations or stages. In the first operation, as shown in FIG. 1, the knee prosthesis is removed to allow the patient and the infected joint to be treated with antibiotics over a period of time, e.g., 6 to 12 weeks. An antibiotic-loaded spacer is inserted in the joint space to maintain a certain amount of joint stability and mobility after the infected prosthesis is removed. After eradication of the infection, a second surgery is performed to implant a revision knee prosthesis.

There are two types of antibiotic-loaded cement spacers: static and articulating. Referring to FIG. 2, a static spacer 10 creates a temporary arthrodesis with antibiotic-loaded bone cement (e.g., PMMA) and are typically handmade during surgery. Typically, a rigid intramedullary rod 12 is placed within the femur and tibia to span across the joint space. Referring to FIG. 3, an articulating spacer, generally indicated at 20, is typically pre-manufactured or pre-formed as femoral and tibial spacer components 24, 26, respectively, manufactured from antibiotic-loaded bone cement. The spacer components 24, 26 are secured to the respective bones using bone cement 28, for example.

BRIEF DESCRIPTION OF THE DRAWINGS

FIG. 4 is a front elevation of an illustrated embodiment of an assembled hinged articulating spacer system for revision knee arthroplasty constructed according to the teachings of the present disclosure.

FIG. 5 is a left side elevation of the hinged articulating spacer system in FIG. 4.

FIG. 16A is a front elevation of a knee joint after removal of a TKA prosthesis and insertion of femur and tibia rods into the femur and tibia, respectively.

FIG. 16B is similar to FIG. 16A with femoral and tibial spacer components inserted into the joint space.

FIG. 16C is similar to FIG. 16B with the femur and tibia rods hingedly coupled to one another to assemble the hinged articulating spacer system and bone cement added within the joint space.

DETAILED DESCRIPTION OF THE DISCLOSURE

Figure 1:
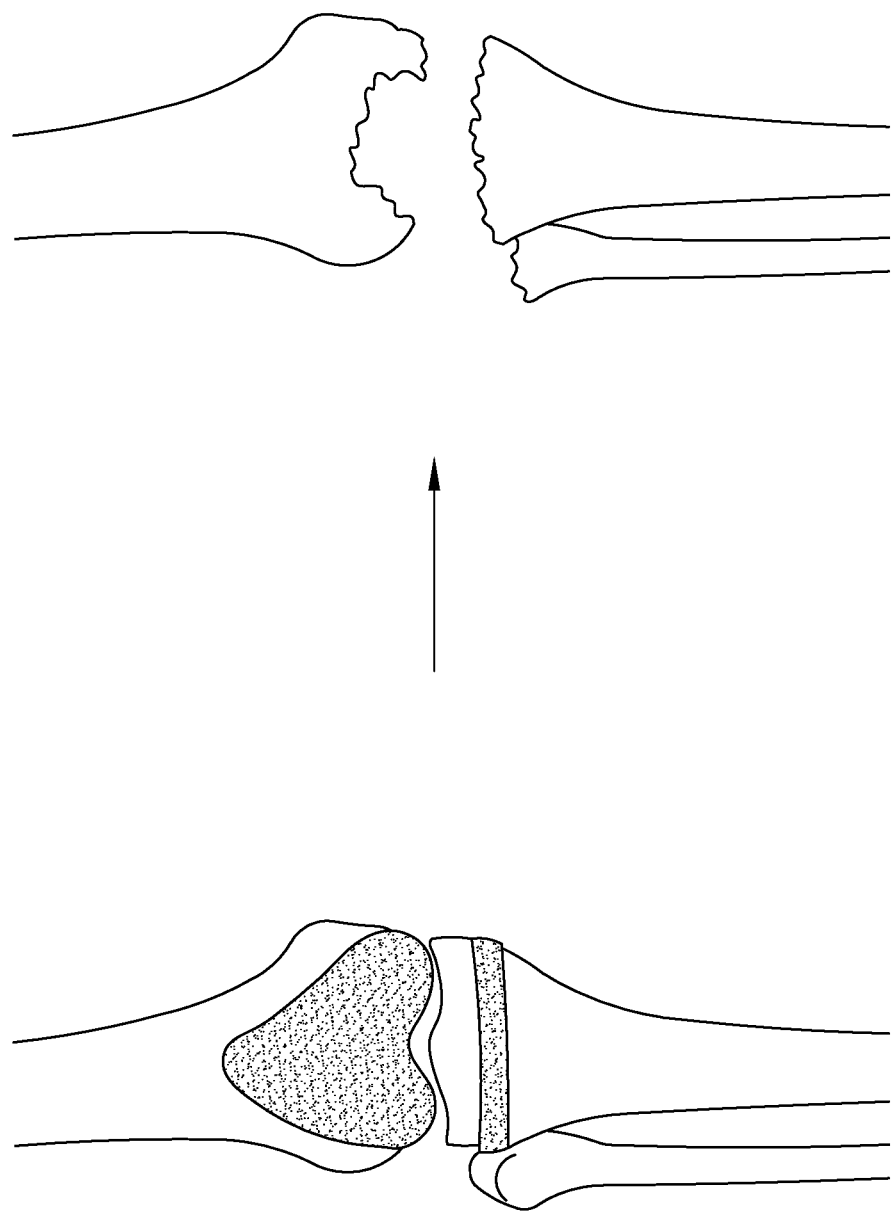
FIG. 1 is a diagram illustrating a conventional surgical procedure of removing an infected total knee arthroplasty (TKA) prosthesis.
Figure 2:
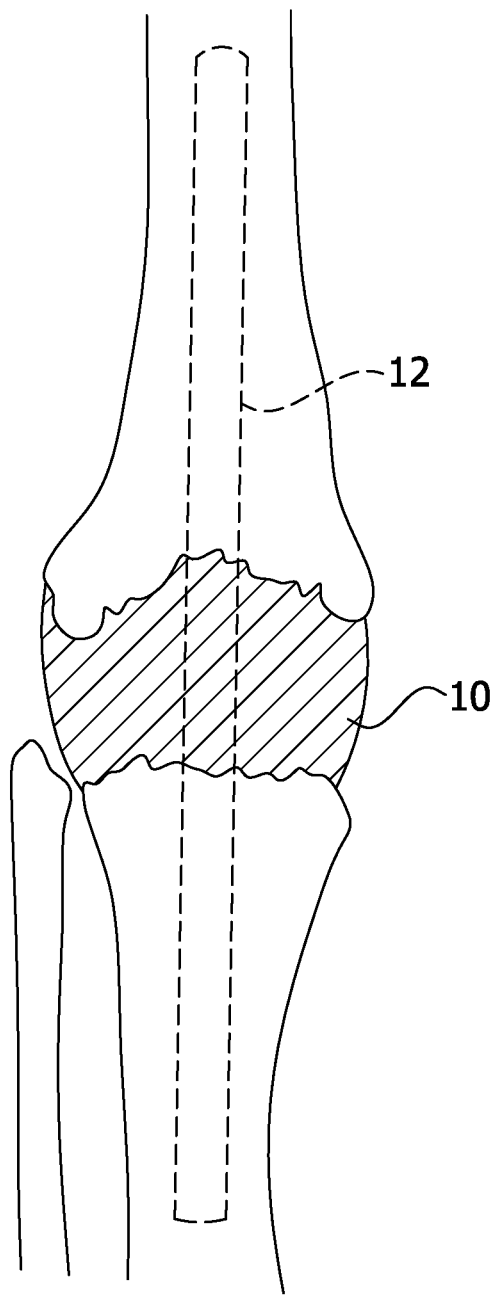
FIG. 2 is a front elevation of a prior art static spacer and rigid rod implanted in a knee after removing a TKA prosthesis.
Figure 3:
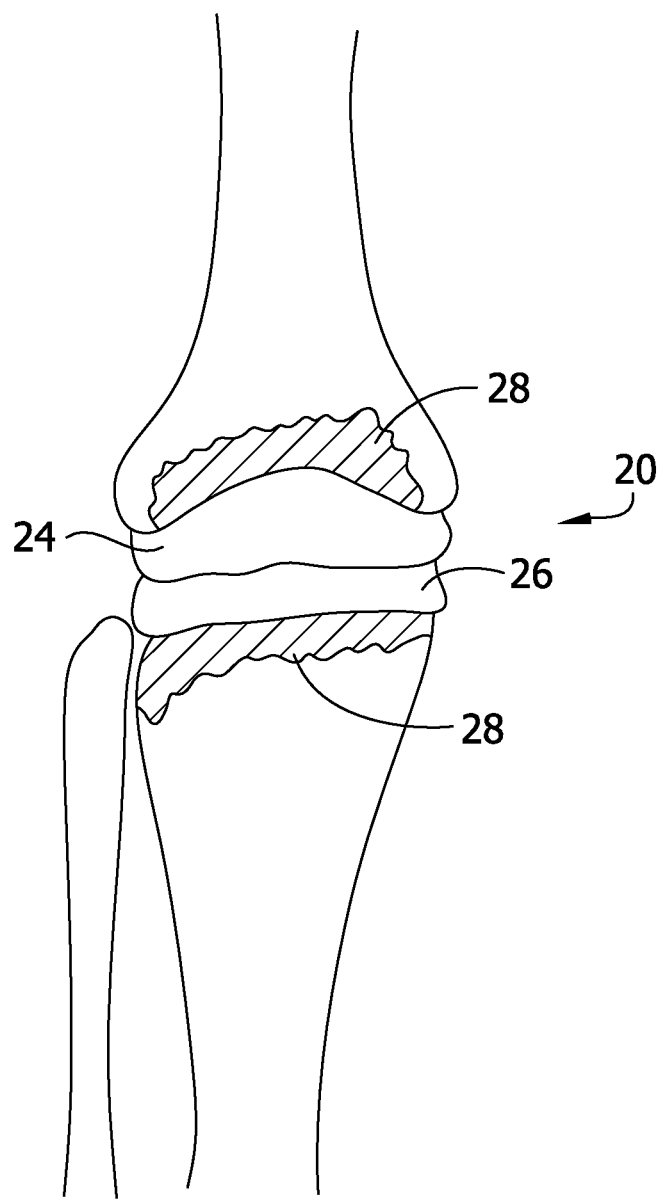
FIG. 3 is a front elevation of a prior art articulating spacer implanted in a knee after removing a TKA prosthesis.
Figure 6:
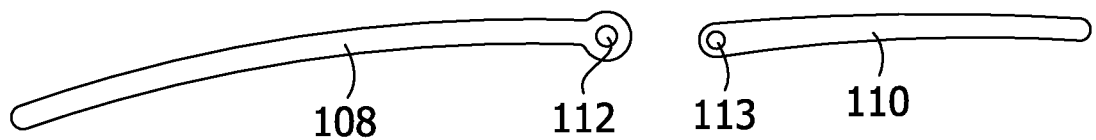
FIG. 6 is an exploded side elevation of a hinged rod assembly of the hinged articulating spacer system, including a femur rod and a tibia rod.

Referring to FIGS. 4 and 5, an illustrated embodiment of a hinged articulating spacer system for revision knee arthroplasty constructed according to the teachings of the present disclosure is generally indicated at reference numeral 100. The hinged articulating spacer system 100 generally comprises a hinged rod assembly, generally indicated at 102, and an articulating component assembly, generally indicated at 104. In FIGS. 4 and 5, the hinged articulating spacer system 100 is assembled. As explained in more detail below, the hinged articulating spacer system 100 is suitable for use in two-stage revision TKA. More specifically, the spacer system 100 is implanted after removing the infected knee prosthesis to allow for antibiotic treatment of the infected jointed space (e.g., 6 to 12 weeks) before performing the revision TKA. The spacer system 100 allows range of motion of the knee, unlike the static spacer, such as shown in FIG. 2. Further, the spacer system 100 inhibits dislocation of the knee joint, unlike a conventional articulating spacer, such as shown in FIG. 3. It is believed the implantation of the spacer system 100 allows for better weight bearing than the articulating spacer, such that motion, pain control and subsequent surgical exposure may be better than the conventional articulating spacer.

Figure 7:
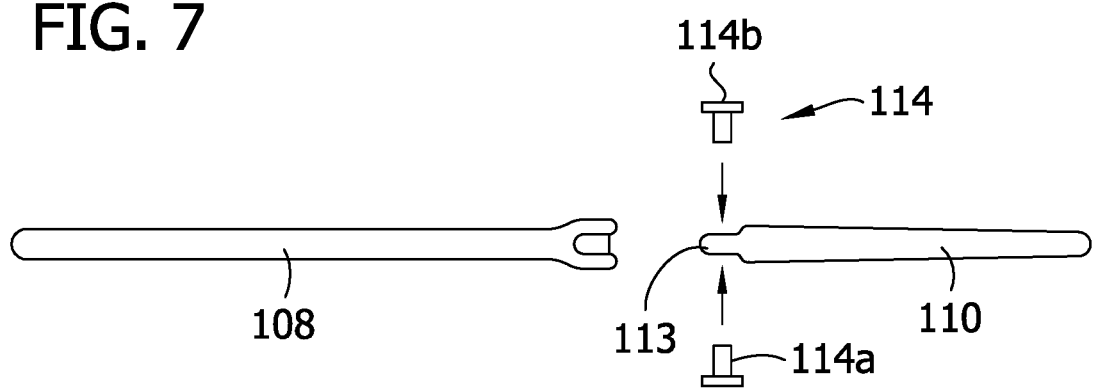
FIG. 7 is an exploded rear elevation of the hinged rod assembly, including an exploded hinge pin removed from the hinged rod assembly.
Figure 8:
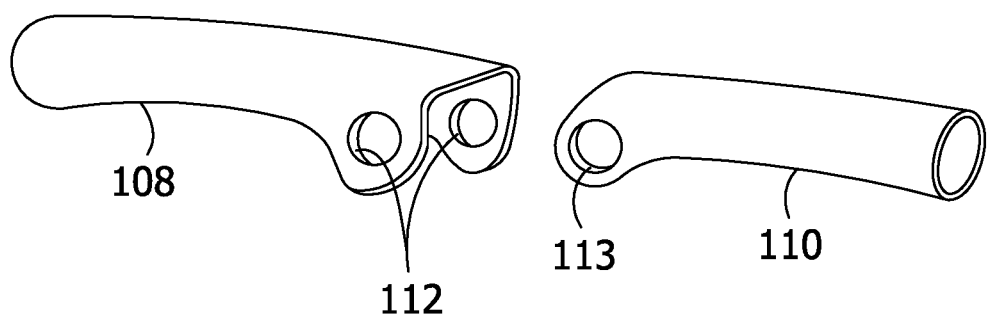
FIG. 8 is an enlarged, fragmentary exploded perspective of the hinged rod assembly showing the distal and proximal ends of the femur and tibia rods, respectively.

Referring to FIGS. 4-8, the hinged rod assembly 102 generally comprises a femur rod 108, and a tibia rod 110 hingedly coupled to the femur rod at a hinged joint to allow rotational or pivoting motion of the tibia rod relative to the femur rod about a transverse rotational axis A (FIG. 4). As seen best in FIG. 8, the distal end of the femur rod 108 has a first coupler (e.g., a fork coupler) hingedly couplable with a second coupler (e.g., a male coupler) at a proximal end of the tibia rod 110. In the illustrated embodiment, the first and second couplers define aligned transverse openings 112, 113, respectively, through which a hinge pin, generally indicated at 114 in FIG. 7, is inserted to allow rotational movement of the tibia rod 110 relative to the femur rod 108 about the transverse rotational axis A. In one or more embodiments, the femur rod 108 and the tibia rod 110 may be formed from, for example, one or more of metal, PMMA (Poly(methyl methacrylate)) (e.g., coated with PMMA), polyethylene, other suitable materials, and combinations thereof.

Figure 9A:
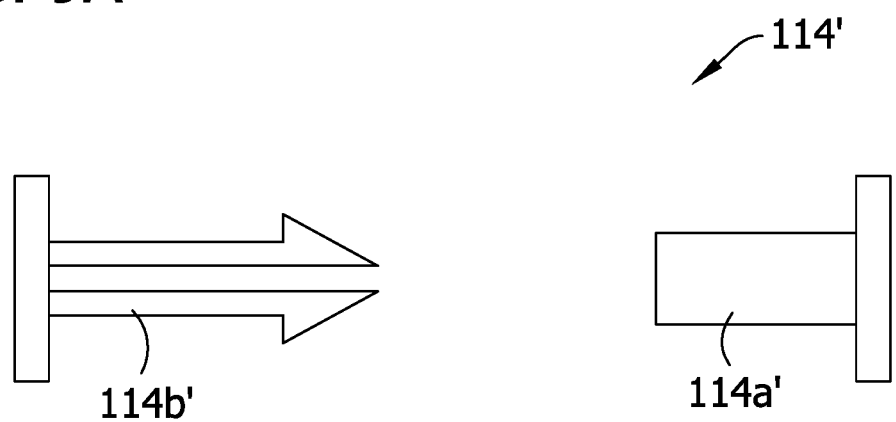
FIG. 9A is an exploded side elevation of another embodiment of hinge pin for the hinged rod assembly.
Figure 9B:
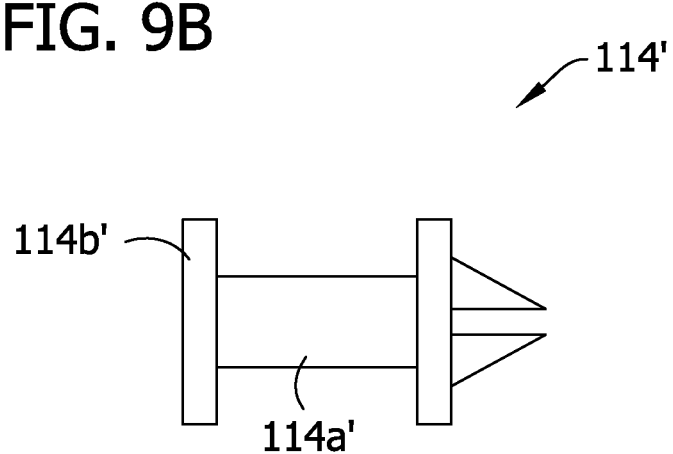
FIG. 9B is a side elevation of the assembled hinge pin in FIG. 9A.
Figure 10:
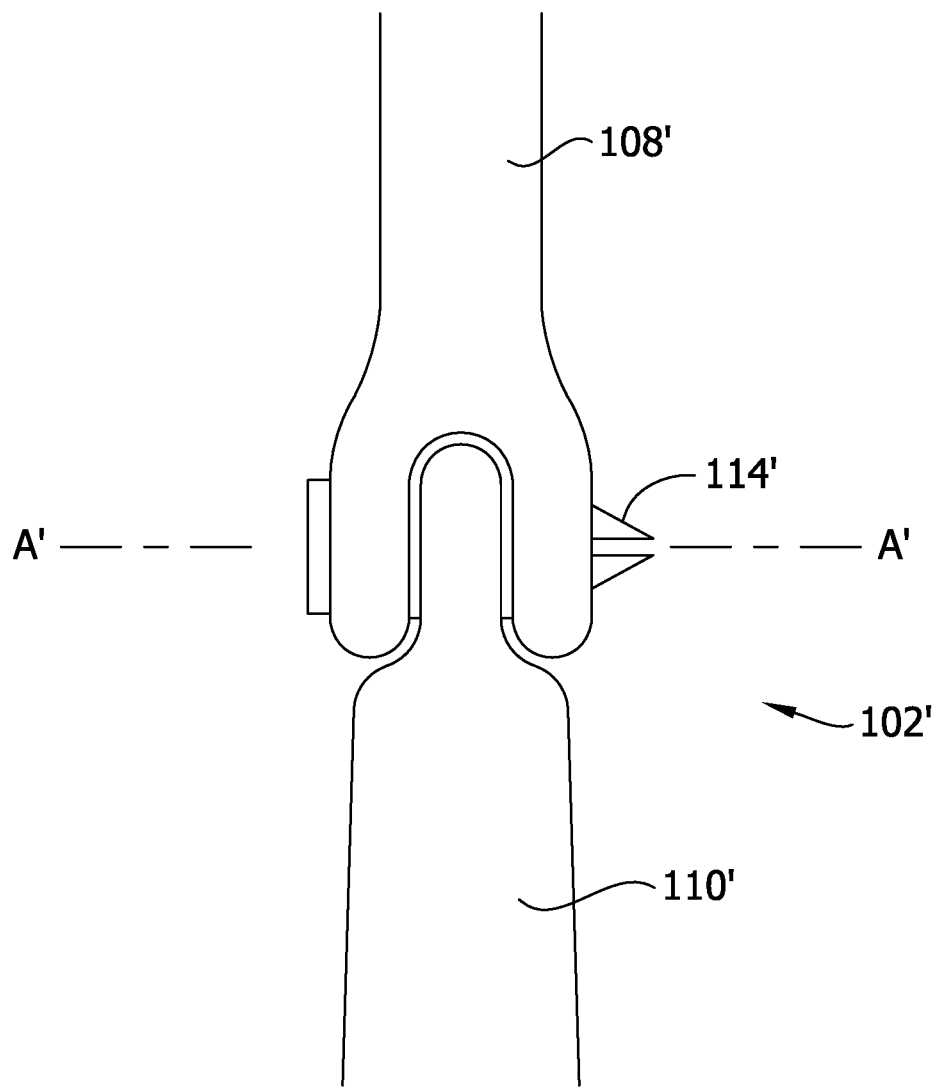
FIG. 10 is a front elevation of another embodiment of a hinged rod assembly.
Figure 11A:
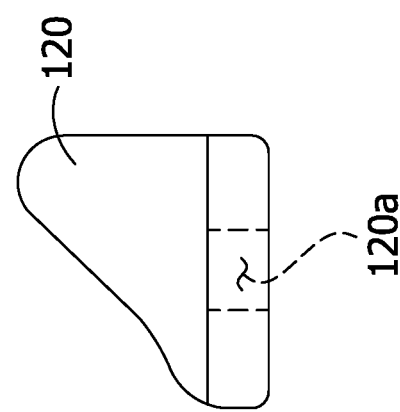
FIG. 11A is a front elevation of a femoral spacer component of an articulating component assembly of the hinged articulating spacer system.
Figure 11B:
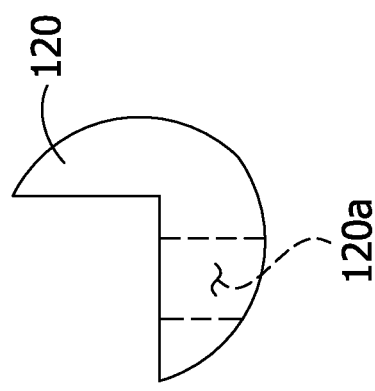
FIG. 11B is a left side elevation of the femoral spacer component in FIG. 11A.
Figure 11C:
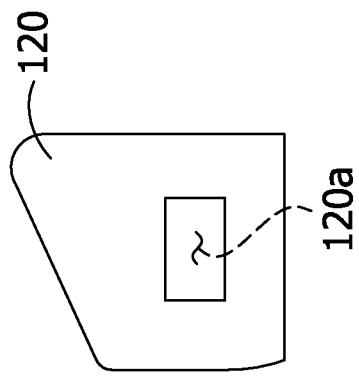
FIG. 11C is a top plan view of the femoral spacer component in FIG. 11A.
Figure 12A:
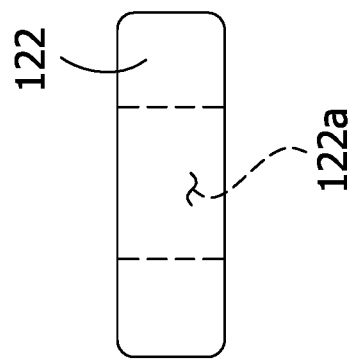
FIG. 12A is a front elevation of a tibial spacer component of the articulating component assembly of the hinged articulating spacer system.
Figure 12B:
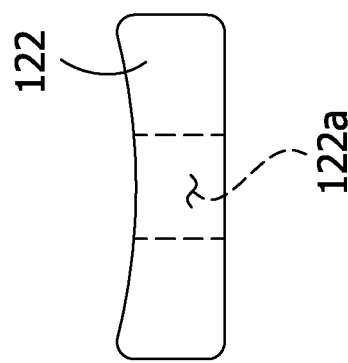
FIG. 12B is a left side elevation of the tibial spacer component in FIG. 11A.
Figure 12C:
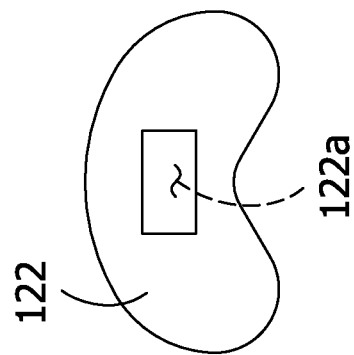
FIG. 12C is a top plan view of the tibial spacer component in FIG. 11A.

The hinge pin 114 may be of suitable design and construction. In one or more embodiments, such as shown in FIG. 7, the hinge pin 114 comprises a cylindrical bearing 114a having a first end shoulder or stop, and a retainer 114b having a second end shoulder or stop. The cylindrical bearing 114a is internally threaded to threadably mate with external threading on a shaft of the retainer 114b to form the hinge pin 114. The end shoulders retain the hinge pin within the couplers of the femur and tibia rod 108, 110. In one or more embodiments, such as shown in FIGS. 9A and 9B, a hinge pin 114' may include a cylindrical bearing 114a' having an end shoulder or stop, and a snap-fit retainer 114b' including cantilevered snap-fit arms and an end shoulder or stop. The snap-fit arms are slidably insertable into the cylindrical bearing 114a' and secured therein by snap-fit connection, as shown in FIG. 9B, to form the hinge pin 114'. The end shoulders retain the hinge pin 114' within the couplers of the femur and tibia rods 108, 110. In one or more embodiments, the hinge pin may be a hinge pin secured in the aligned openings of the femur and tibia rods 108, 110 by a cotter pin or retaining ring, as is generally known. The femur and tibia rods 108, 110 may be hingedly couplable to one another in other ways. For example, in FIG. 10 another hinged rod assembly 102' comprises a femur rod 108', and a tibia rod 110' hingedly coupled to the femur rod at a hinged joint to allow rotational or pivoting motion of the tibia rod relative to the femur rod about a transverse rotational axis A'. The hinged rod assembly 102' is similar to the hinged rod assembly 102 and functions, in operation, in essentially the same way. The distal end of the femur rod 108' has a first coupler (e.g., a fork coupler) hingedly couplable with a second coupler (e.g., a male coupler) at a proximal end of the tibia rod 110'. In the illustrated embodiment, the first and second couplers define aligned transverse openings through which a hinge pin, generally indicated at 114', is inserted to allow rotational movement of the tibia rod 110' relative to the femur rod 108' about the transverse rotational axis A'. Compared to the hinged rod assembly 102, the fork coupler of the femur rod 108' of the present hinged rod assembly 102' has struts or tines that have a greater thickness than struts or tines of the other hinged rod assembly 102. Moreover, the hinge pin 114' in this embodiment may comprise a single component having a snap-fit connector that "snaps" directly onto the distal end of the femur rod 108', rather than a two-piece component as shown in FIGS. 9A and 9B, for example.

Figure 13:
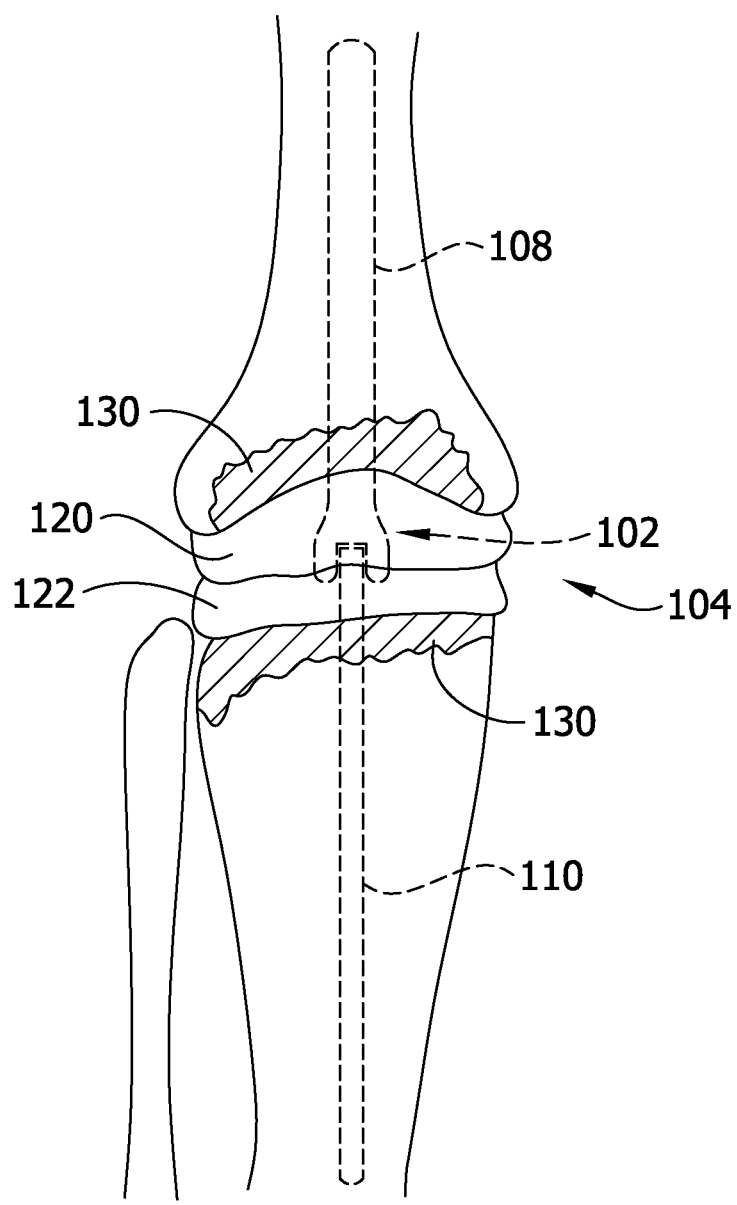
FIG. 13 is a front elevation of the hinged articulating spacer system implanted in a knee after removal of a TKA prosthesis, a superior segment of an anterior portion of the femoral spacer component being broken off to show underlying bone cement.
Figure 14:
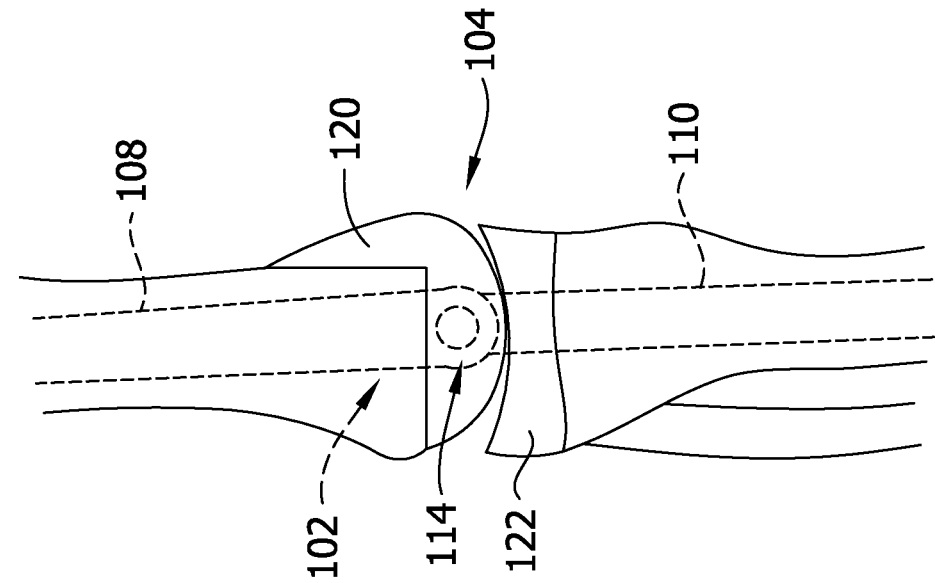
FIG. 14 is similar to FIG. 13, except the femoral spacer component is shown in full.
Figure 15:
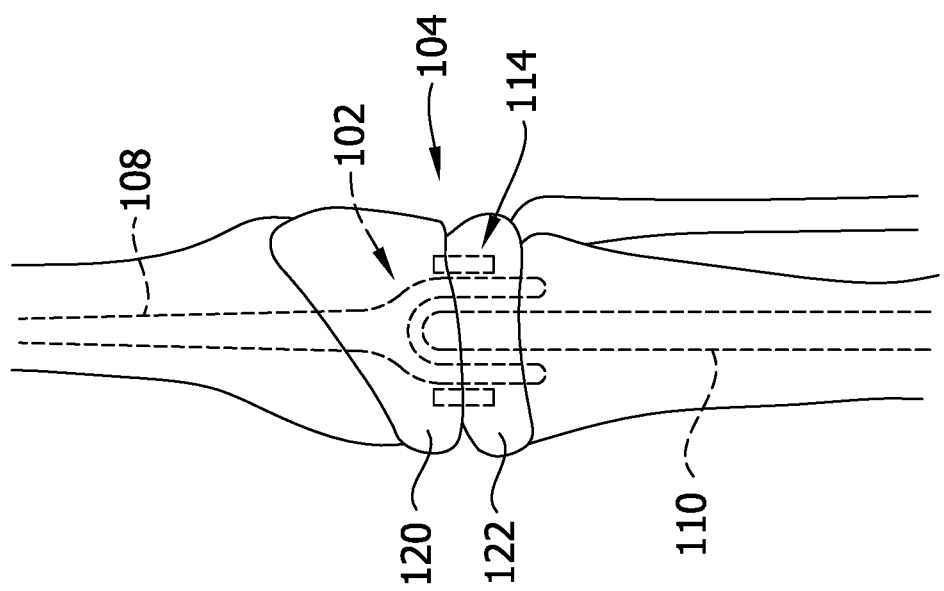
FIG. 15 is a left side elevation of FIG. 14.
Figure 17A:
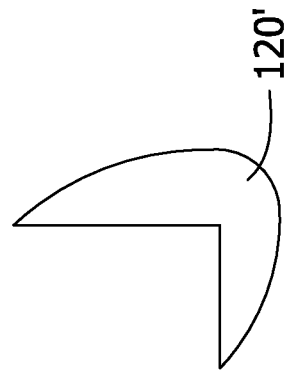
FIG. 17A is a front elevation of another embodiment of a femoral spacer component for the hinged articulating spacer system.
Figure 17B:
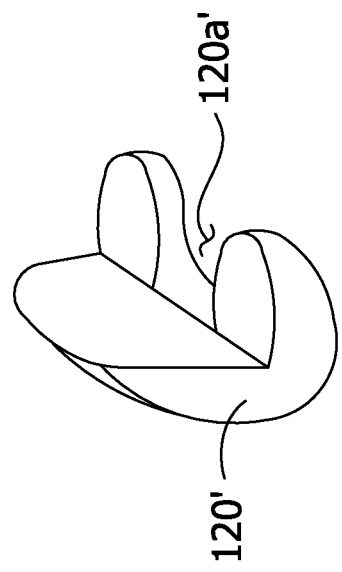
FIG. 17B is a side elevation of the femoral spacer component in FIG. 17A.
Figure 17C:
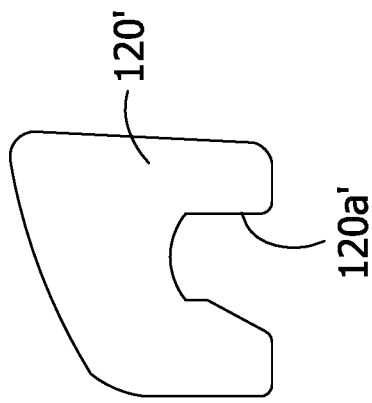
FIG. 17C is a top plan view of the femoral spacer component in FIG. 17A.
Figure 17D:
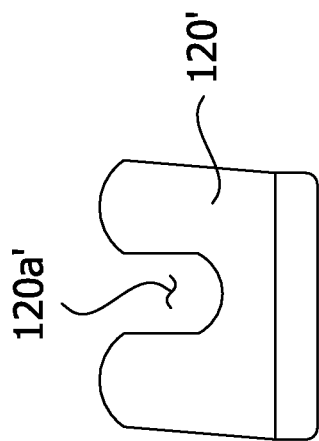
FIG. 17D is a rear perspective of the femoral spacer component in FIG. 17A.

Referring to FIGS. 13-15, the femur rod 108 is configured to be inserted into the medullary canal of the femur. The tibia rod 110 is configured to be inserted into the medullary canal of the tibia. As explained in more detail below, when the femur and tibia rods 108, 110 are inserted into the respective medullary canals of the femur and tibia, the axis of the hinged joint is located generally at the rotational axis of the knee to allow at least limited extension and flexion of the knee. Moreover, the hinged rod assembly 102 (e.g., the hinge joint) may bear at least some of the load at the knee joint. The femur and tibia rods 108, 110 may be constructed of suitable biocompatible material that is generally rigid. For example, the rods 108, 110 may be formed from stainless steel, titanium, or other materials. In one or more embodiments, the body or shaft of the femur rod 108 may have a diameter from about 10 mm to about 16 mm, or other suitable diameters or cross-sectional dimensions. In one or more embodiments, the femur rod 108 may have a length from about 150 mm to about 200 mm, or other suitable lengths. In one or more examples, the body or shaft of the tibia rod 110 may have a diameter from about 10 mm to about 14 mm, or other suitable diameters or cross-sectional dimensions. In one or more embodiments, the tibia rod 110 may have a length of about 150 mm, or other suitable lengths.

Referring to FIGS. 4, 5 and 11A-12C, the articulating component assembly 104 generally comprises a femoral spacer component 120 and a tibial spacer component 122. The femoral spacer component 120 is configured to be secured to the distal end of the femur, such as by bone cement (e.g., PMMA (Poly(methyl methacrylate))), which may be pre-loaded with antibiotics. The femoral spacer component 120 may be pre-formed (i.e., pre-manufactured) from bone cement (e.g., PMMA) and impregnated with antibiotics (e.g., gentamicin), similar to conventional articulating spacers. The femoral spacer component 120 may have a shape similar to conventional femoral articulating spacers and/or TKA femoral spacer components or may have other suitable shapes. The tibial spacer component 122 is configured to be secured to the proximal end of the tibia, such as by bone cement (e.g., PMMA), which may be pre-loaded with antibiotics. The tibial spacer component 122 may be pre-formed (i.e., pre-manufactured) from bone cement (e.g., PMMA) and impregnated with antibiotics (e.g., gentamicin), similar to conventional tibial articulating spacers. The tibial spacer component 122 may have a shape similar to conventional tibial articulating spacers and/or TKA tibial spacer components or may have other suitable shapes. When implanted, respective articular surfaces of the femoral and tibial spacer components 120, 122 engage one another through range of motion of the knee while bearing at least some load.

As shown in FIG. 11A-12C, unlike conventional articulating spacers, the femoral and tibial spacer components 120, 122 define openings 120a, 122a, e.g., through openings, recesses, or clearances, in or through which the hinged rod assembly 102 is received. In the illustrated embodiment, only the tibia rod 110 extends through the openings 120a, 122a such that the hinged joint of the hinged rod assembly 102 is superior to the openings. In one or more other embodiments, the hinged joint of the hinged rod assembly 102 may be received in the openings 120a, 122a such that the openings provide clearance for the hinged joint through range of motion of the knee. It is understood that the hinged joint of the hinged rod assembly 102 may be disposed at any location relative to the openings 120a, 122a of the femoral and tibial spacer components 120, 122 that is suitable for allowing at least some range of motion of the hinged rod assembly 102 and the knee joint. Another embodiment of a femoral spacer component is generally indicated at reference numeral 120'. In this embodiment, the femoral spacer component 120' defines a notch 120a' or recess extending from a posterior end of the component. This is slightly different than the through opening 120a of the femoral spacer component 120. Other configurations of the opening 120a, 120a' are possible.

Referring to FIGS. 16A-16C, in one or more embodiments, the hinged articulating spacer system 100 is utilized in a two-stage revision TKA. As shown in FIG. 16A, in a first step, the femoral and tibial TKA components are removed from the patient. As is known, in general the joint space is cleaned, and remaining bone cement and necrotic debris and bone tissue is removed, leaving a large joint space between the femur and tibia. Next, one or both of the femur rod 108 and the tibial rod 110 are individually inserted into the respective medullary canals of the femur and tibia. That is, the femoral and tibial rods may be unattached when inserted into the respective bones. Bone cement may be used to secure the femoral and tibial rods 108, 110 to the respective femur and tibia. Other ways of fixing the rods to the respective bones may be used. For example, the rods may include friction-enhancing structures, such as teeth or ribs or knurls, for increasing friction and inhibiting axial movement of the hinged rod assembly 102 within the medullary canals.

The femoral and tibial spacer components 120, 122 are inserted into the joint space and after insertion of the femur and tibia rods 108, 110, respectively. For example, as shown in FIG. 16B, the femoral spacer component 120 may be placed on the distal end of the femur such that the femur rod 108 is received in the opening 120a of the femoral spacer component 120, and the tibial spacer component 122 may be placed on the proximal end of the tibia such that the tibia rod 110 is received in the opening 122a of the tibial spacer component. Bone cement may be applied to the respective ends of the femur and the tibia and/or of the respective surfaces of the femoral and tibial rods to facilitate coupling of the components to the respective bones. In another example, the tibia rod 110 may be inserted through the openings 120a, 122a of both the tibial and femur components 122, 120, such as in an embodiment where the femur component is not inserted into the opening of the femur, such as shown in FIGS. 4 and 5.

With the rods 108, 110 in place and the femoral and tibial spacer components 120, 122 in the joint space, the femur and tibia rods are then hingedly coupled to one another, such as by bringing the respective couplers together and inserting the hinge pin 114 through aligned transverse openings 112, 113 in the couplers. At this time, the articular surfaces of the femoral and tibial spacer components 120, 122 may contact and engage one another. Bone cement 130 may be applied to bone defects in the femur and tibia. Moreover, additional bone cement may be applied to facilitate proper seating and securement of the femoral and tibial spacer components 120, 122 on the respective bones.

In the second stage of the revision TKA, the hinged articulating spacer system 100 is removed, typically 6 to 12 weeks after implantation. The revision TKA system is then implanted. Thus, the hinged articulating spacer system 100 is only temporary and used to facilitate eradication of the infection.

It is believed that the teachings set forth in the present disclosure provide a hinged articulating spacer system that allows for range of motion of the knee joint while inhibiting dislocation of the joint during the infection-treatment time of a two-stage revision TKA. Thus, it is believed the patient is more mobile and ambulatory, with reduced pain and risks of dislocation of knee joint, compared to both the static spacer and the articulating spacer. This further leads to a better quality of life for the patient and increases success of the second stage of the revision TKA.

Modifications and variations of the disclosed embodiments are possible without departing from the scope of the invention defined in the appended claims.

When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A hinged articulating spacer system for revision knee arthroplasty comprising:
    a femur rod configured to be inserted into a distal end of a femur;
    a tibia rod configured to be inserted into a proximal end of a tibia, wherein the tibia rod is configured to be hingedly coupled to the femur rod to form a hinged rod assembly;
    a hinge coupler configured to hingedly couple the femur and tibia rods to one another to form the hinged rod assembly;
    a pre-formed femoral spacer component including bone cement impregnated with an antibiotic, the pre-formed femoral spacer defining an opening configured to receive the hinged rod assembly; and
    a pre-formed tibial spacer component including bone cement impregnated with an antibiotic, the pre-formed tibial spacer defining an opening configured to receive the hinged rod assembly,
    wherein the femur rod has a distal end defining an opening, wherein the tibia rod has a proximal end defining an opening, wherein the openings of the femur rod and the tibia rod, respectively, are alignable and the hinge coupler is receivable in the openings when the openings are aligned to hingedly couple the tibia rod to the femur rod,
    wherein when assembled the hinged rod assembly extends through the pre-formed femoral and tibial spacer components and allows rotational or pivoting motion of the tibia rod relative to the femur rod about a transverse rotational axis.

2. The hinged articulating spacer system set forth in claim 1, wherein the hinge coupler is a hinge pin configured to hingedly couple the femur and tibia rods to one another to form the hinged rod assembly.

3. The hinged articulating spacer system set forth in claim 2, wherein the hinge pin includes a snap-fit connection.

4. The hinged articulating spacer system set forth in claim 1, wherein the distal end of the femur rod includes a fork coupler defining the opening.

5. The hinged articulating spacer system set forth in claim 4, wherein the proximal end of the tibia rod is insertable between tines of the fork coupler.

6. The hinged articulating spacer system set forth in claim 1, wherein the femur rod and the tibia rod comprise one or more of metal, PMMA (Poly(methyl methacrylate), polyethylene, and combinations thereof.

7. The hinged articulating spacer system set forth in claim 1, wherein the cement of the pre-formed femoral spacer component and the pre-formed tibial spacer component comprise PMMA (Poly(methyl methacrylate).

8. The hinged articulating spacer system set forth in claim 1, wherein the antibiotic comprises gentamicin.

9. A method of performing a revision total knee arthroplasty using the hinged articulating spacer system set forth in claim 1, the method comprising:
  removing a total knee arthroplasty prosthesis from a knee joint of a patient, thereby creating a joint space;
  inserting, after said removing the total knee arthroplasty prosthesis, the hinged articulating spacer system, wherein said inserting the hinged articulating spacer system includes:
    inserting the femur rod into a distal end of a femur of the knee joint,
    inserting the tibia rod into a proximal end of a tibia of the knee joint,
    inserting the pre-formed femoral spacer component into the joint space,
    inserting the pre-formed tibial spacer component into the joint space, and
    hingedly coupling the femur rod and the tibia rod to one another to assemble the hinged rod assembly, wherein when assembled the hinged rod assembly extends through the pre-formed femoral and tibial spacer components.

10. The method of performing a revision total knee arthroplasty set forth in claim 9, wherein said hingedly coupling the femur rod and the tibia rod to one another comprises inserting the hinge coupler through the femur rod and the tibia rod.

11. The method of performing a revision total knee arthroplasty set forth in claim 10, wherein the hinge coupler is a hinge pin, and wherein said inserting a hinge coupler through the femur rod and the tibia rod comprises inserting the hinge pin through the aligned openings in the femur rod and the tibia rod.

12. The method of performing a revision total knee arthroplasty set forth in claim 11, wherein said hingedly coupling the femur rod and the tibia rod to one another further comprises snap-fitting the hinge pin to secure the hinge pin to the femur rod and the tibia rod.

13. The method of performing a revision total knee arthroplasty set forth in claim 11, wherein a distal end of the femur rod includes a fork coupler.

14. The method of performing a revision total knee arthroplasty set forth in claim 13, wherein said hingedly coupling the femur rod and the tibia rod to one another further comprises inserting a proximal end of the tibia rod between tines of the fork coupler of the femur rod.

15. The method of performing a revision total knee arthroplasty set forth in claim 9, wherein the femur rod and the tibia rod comprise one or more of metal, PMMA (Poly(methyl methacrylate), polyethylene, and combinations thereof.

16. The method of performing a revision total knee arthroplasty set forth in claim 9, wherein the pre-formed femoral spacer component and the pre-formed tibial spacer component comprise PMMA (Poly(methyl methacrylate).

\* \* \* \* \*